United States Patent [19]

Hill et al.

[11] Patent Number: 4,988,186
[45] Date of Patent: Jan. 29, 1991

[54] APPARATUS FOR QUANTIFYING VISUAL FUNCTION DEFECTS

[76] Inventors: Adrian R. Hill, Brewers, Sheepstead, Abingdon, Oxon, OX13 6QG; Arthur E. Burgess, 105 Main Street, Fintry, Glasgow G63 OXE; Barnaby C. Reeves, 72 St Mary's Road, Oxford, all of United Kingdom

[21] Appl. No.: 223,239

[22] Filed: Jul. 25, 1988

[30] Foreign Application Priority Data

Nov. 25, 1986 [GB] United Kingdom ............... 8628178

[51] Int. Cl.⁵ .............................................. A61B 3/02
[52] U.S. Cl. .................................... 351/239; 354/243
[58] Field of Search ............. 351/222, 243, 246, 239; 250/223 R; 235/464

[56] References Cited

U.S. PATENT DOCUMENTS 2,612,994  10/1952  Woodland et al. ............. 250/223 R
3,643,068  2/1972   Mohan et al.
3,918,029  11/1975  Lemelson
4,292,511  9/1981   Heyman et al. ................ 235/464 X

FOREIGN PATENT DOCUMENTS 2500190   12/1982  France.
2098820   11/1982  United Kingdom.
WO88/03776 2/1988  United Kingdom.

OTHER PUBLICATIONS

"Microprocessor Controlled Colour Vision Tester", Pritty, 6/1979.
"The Farnsworth-Munsell 200-Hue Test for the Examination of Color Discrimination", Farnsworth,-1949.
"Recent Developments in Farnsworth's Colour Vision Tests", Taylor et al.,-1976.
"Inter Eye Comparison on the 100 Hue Test", Aspinall,-1974.
"A Modified 100 Hue Test for Use In The Investigation of Glaucoma", Connolly et al.,-1982.
"Instrumentation for the Farnsworth-Munsell 100-hue Test", Donaldson, et al., 2/77.
"The Farnsworth-Munsell 100-Hue and Dichotomous Tests for Color Vision", Farnsworth,-1943.
"Exploitation des Tests de Vision coloree sur ordinateur", Hache et al., 1970.
"Diagnosis and Genetics of Defective Colour Vision", Kalmus,-1965.
"Proposals for Scoring and Assessing the 100-Hue Test", Kinnear,-1970.
"Semilogie Clinique De La Saturation Chromatique", Lanthony,-1977.
"Attempt at a Method of Programmation with Computer IBM 1130 for the Study of Acquired and Hereditary Colour Vision Deficiencies by Means of the Test of Farnsworth", Parra, 1972.
"Congenital and Acquired Color Vision Defects", Pokorny et al., 1979.
"Clinical Experience of Electronic Calculation and Automatic Plotting of Farnsworth's 100-Hue Test", Taylor, 1978.
"Further Studies on Acquired Deficiency of Color Discrimination", Verriest, 1/1963.
"A New Assessment of the Normal Ranges of the Farnsworth-Munsell 100-Hue Test Scores", Verriest, 1982.
"The Lightness Discrimination Test", Verriest et al., 1979.

*Primary Examiner*—Rodney B. Bovernick
*Attorney, Agent, or Firm*—Dickstein, Shapiro & Morin

[57] ABSTRACT

Apparatus for quantifying visual function defects comprises a plurality of testing elements (1) having a surface (3) provided with a selected visual stimulus (5) and with a machine readable code (6) for uniquely identifying the stimulus (5). The apparatus further comprises a light pen (12) for reading the code (6) on each element (1) and a microprocessor (20) for analysing the codes (6) read by the light pen (12) in order to quantify the visual function defect.

19 Claims, 5 Drawing Sheets

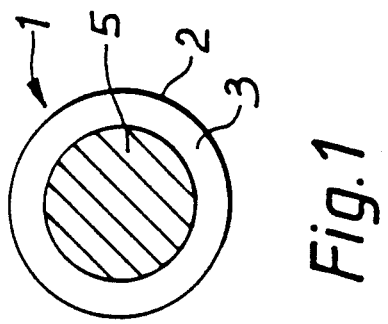
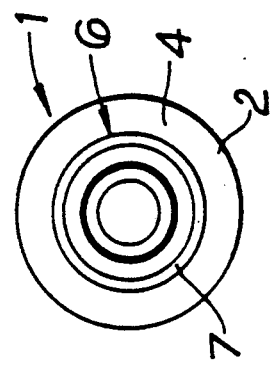
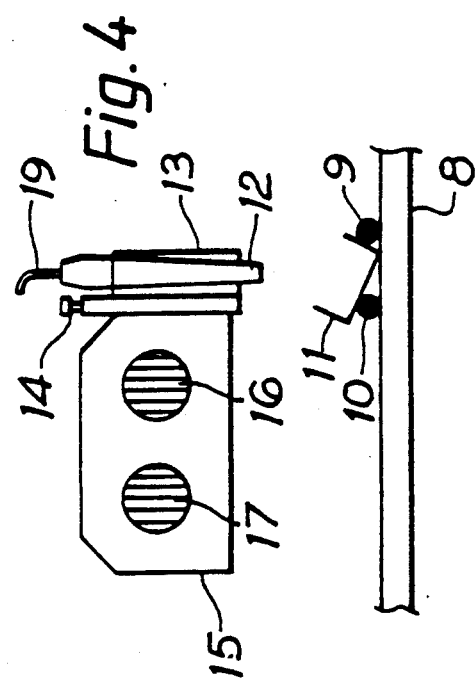
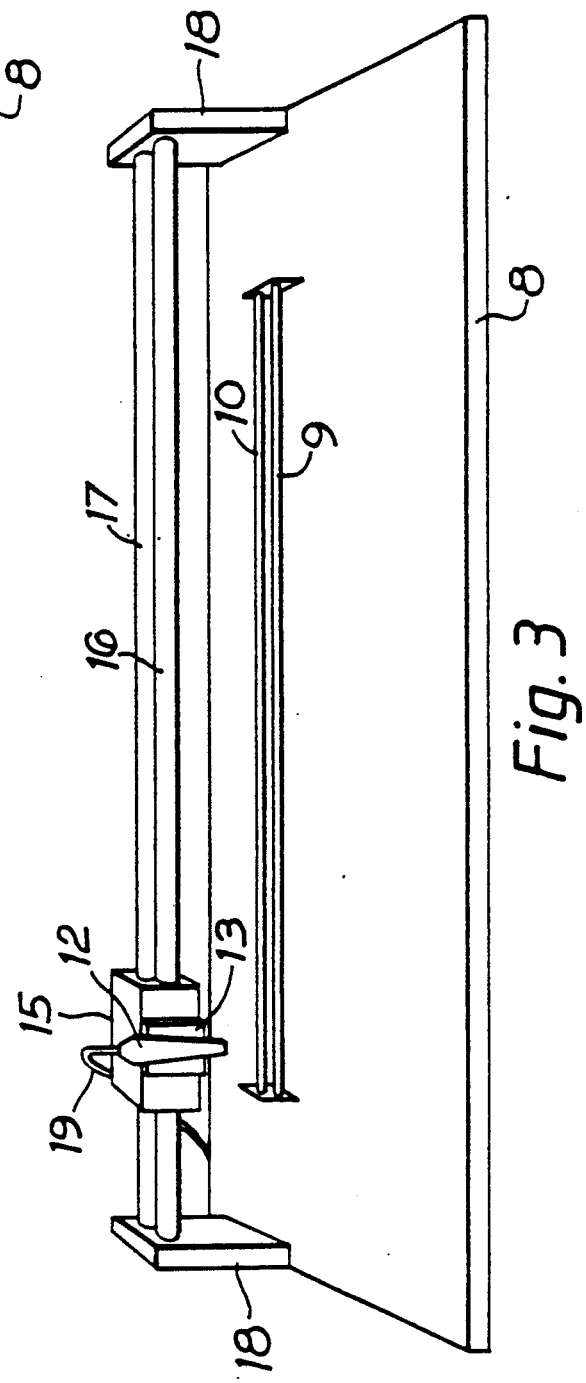

NAME=REEVES BC
HOSP. NO. = 123456
D.O.B. =07/09/55
RIGHT EYE

| | | | |
|---|---|---|---|
| 1 | 9 | T | TTTTT |
| 2 | 6 | . | xxx |
| 3 | 2 | . | x |
| 4 | 9 | . | xxxxx |
| 5 | 16 | . | xxxxxxx |
| 6 | 12 | . | xxxxx |
| 7 | 5 | . | xxx |
| 8 | 7 | . | xxxx |
| 9 | 5 | . | xxx |
| 10 | 3 | . | xx |
| 11 | 3 | . | xx |
| 12 | 1 | S | S |
| 13 | 2 | . | x |
| 14 | 5 | . | xxx |
| 15 | 8 | D | DDDD |
| 16 | 5 | . | xxx |
| 17 | 1 | . | x |
| 18 | 0 | . | |
| 19 | 2 | P | P |
| 20 | 3 | . | xx |
| 21 | 3 | . | xx |
| 22 | 3 | . | xx |
| 23 | 1 | . | x |
| 24 | 1 | . | x |
| 25 | 1 | . | x |
| 26 | 0 | . | |
| 27 | 0 | . | |
| 28 | 2 | . | x |
| 29 | 2 | . | x |
| 30 | 2 | . | x |
| 31 | 2 | . | x |
| 32 | 2 | . | x |
| 33 | 2 | . | x |
| 34 | 0 | . | |
| 35 | 0 | . | |
| 36 | 1 | . | x |
| 37 | 1 | . | x |
| 38 | 1 | . | x |
| 39 | 1 | . | x |
| 40 | 0 | . | |
| 41 | 0 | . | |
| 42 | 0 | . | |
| 43 | 0 | . | |
| 44 | 0 | . | |
| 45 | 1 | . | x |
| 46 | 1 | . | x |
| 47 | 1 | T | T |
| 48 | 1 | . | x |
| 49 | 1 | . | x |
| 50 | 1 | . | x |
| 51 | 1 | . | x |
| 52 | 3 | . | xx |
| 53 | 2 | . | x |
| 54 | 0 | S | |
| 55 | 0 | . | |
| 56 | 0 | . | |
| 57 | 2 | . | x |
| 58 | 3 | . | xx |
| 59 | 1 | D | D |
| 60 | 1 | . | x |
| 61 | 1 | . | x |
| 62 | 0 | . | |
| 63 | 3 | . | xx |
| 64 | 3 | . | xx |
| 65 | 2 | P | P |
| 66 | 2 | . | x |
| 67 | 1 | . | x |
| 68 | 7 | . | xxxx |
| 69 | 7 | . | xxxx |
| 70 | 3 | . | xx |
| 71 | 3 | . | xx |
| 72 | 5 | . | xxx |
| 73 | 6 | . | xxx |
| 74 | 6 | . | xxx |
| 75 | 6 | . | xxx |
| 76 | 3 | . | xx |
| 77 | 5 | . | xxx |
| 78 | 5 | . | xxx |
| 79 | 5 | . | xxx |
| 80 | 5 | . | xxx |
| 81 | 3 | . | xx |
| 82 | 2 | . | x |
| 83 | 2 | . | x |
| 84 | 9 | . | xxxxx |
| 85 | 10 | . | xxxxx |

TOT. ERROR SCORE= 252
5% CONF. LIM. = 106
1% CONF. LIM. = 134
BOX 1 SCORE= 117
BOX 2 SCORE= 22
BOX 3 SCORE= 23
BOX 4 SCORE= 90
RES. ABNORMAL. P<1%
FELLOW EYE SCORE= 196
DIFF. BETWEEN EYES
NOT SIGNIFICANT

*Fig. 10*

APPARATUS FOR QUANTIFYING VISUAL FUNCTION DEFECTS

BACKGROUND OF THE INVENTION

1. Field of the Invention

This invention relates to apparatus for quantifying visual function defects. The invention also relates to a testing element for use in quantifying visual function defects. The apparatus and testing element are particularly applicable to the detection of colour vision defects.

2. Description of the Prior Art

There are a number of known methods of testing eye defects.

For example, in testing colour blindness the FM (Farnsworth-Munsell) 100 Hue test is of considerable value in the detection and diagnosis of acquired dyschromatopsias and in providing a means of classification of congenital colour vision deficiences. The test is described in detail in the following articles: "The Farnsworth-Munsell 100 Hue Test and Dichotomous Tests for Color Vision" by D. Farnsworth in the Journal of the Optical Society of America, volume 33, No. 10, October 1953, pages 568 to 578; and "The Farnsworth-Munsell 100 Hue Test for the Examination of Color Discrimination", a manual by D. Farnsworth published in 1949 by the Munsell Color Company Inc.

In this test a plurality of coloured discs are arranged in a selected order by a subject being tested. The discrepancies between the selected order and the correct order can be analysed to provide a reliable diagnosis of the subject's colour vision defects.

Unfortunately the analysis is time consuming and for this reason the FM 100 Hue Test is unpopular in clinics.

A computerised testing apparatus has been devised and this is described in the following articles: "Recent Developments in Farnsworth's. Colour Vision Tests" by W. O. G. Taylor et al in the Transactions of the Ophthalmic Society UK, volume 96, 1976, pages 262 to 264; and in "Instrumentation for the Farnsworth-Munsell 100 Hue Test" by G. B. Donaldson in the Journal of the Optical Society of America, volume 67, No. 2, February 1977, pages. 248 and 249. These devices use differentially coded resistors which identify each particular coloured disc.

The computerised apparatus. considerably reduces the time involved in analysing the test results, but unfortunately is extremely expensive.

SUMMARY OF THE INVENTION

It is an object of the present invention to provide improved apparatus for quantifying visual function defects particularly for testing colour vision defects.

It is a further object of the invention to provide apparatus for quantifying visual function defects which is much simpler and easier to use than has previously been possible.

It is a further object of the invention to provide apparatus for quantifying visual function defects in which the risk of operator error is much smaller than has previously been possible.

According to one aspect of the invention there is provided apparatus for quantifying visual function defects comprising a plurality of testing elements having a surface provided with a selected visual stimulus and with identification means. comprising a machine readable code for uniquely identifying the selected visual stimulus, reading means for reading the code on the surface of each element, and microprocessing means adapted to analyse the code read by the reading means to quantify the visual function defect.

Advantageously the code is such that it can be read by passing the reading means over the surface of the testing elements in any direction. This enables the reading means to read the code regardless of the orientation of the testing elements.

Preferably the code comprises a plurality of substantially circular lines of predetermined thickness and spacing said predetermined thickness and spacing being such as to identify uniquely the selected visual stimulus on the surface of the testing element.

Advantageously the apparatus further comprises a testing element receptacle for receiving said testing elements. Preferably the receptacle is elongate and is adapted to receive the elements arranged in a single row.

Desirably the apparatus further comprises first support means for supporting said testing elements at a first predetermined position. The support means may comprise at least one support element for supporting the receptacle at the first predetermined position.

Desirably also, the apparatus further comprises second support means for supporting the reading means at a second predetermined position.

The second support means preferably includes guide means for guiding movement of the reading means relative to the testing elements along a first axis.

The testing elements and the elongate receptacle may be arranged along the first axis.

In use, the testing elements are arranged in the receptacle by a test subject and the sequence in which the subject arranges the elements can be analysed to determine whether the subject has any eye defect.

The apparatus is particularly useful as apparatus for testing colour vision defects using the FM 100 hue test described above. In this case each selected visual stimulus will comprise a selected colour provided over at least part of the surface of each testing element.

The apparatus according to the invention can be sold in the form of a complete tester for the FM 100 Hue Test, or can be sold as an accessary for use with existing FM 100 Hue Test components.

Preferably each testing element comprises a disc having the visual stimulus provided on one face thereof, and having the code provided on an opposite face thereof.

The testing elements may be of any desired configuration. However, circular, quadrilateral, pentagonal or hexagonal configuratons are preferred.

If the code is not capable of being read in any direction, then it is preferred that alignment means is provided on the elements and the receptacle so that they can only be placed in the receptacle at a predetermined orientation. This orientation can be selected such that all the codes can be read by a single movement of the reading means along the row of the testing elements.

The code is preferably capable of being read by optical reading means in which case the reading means may comprise a light pen. However, it is possible for the code to be of a magnetic nature. Alternatively, the code may be ultraviolet sensitised in which case the reading means would be an ultraviolet sensitive detector.

The micoprocessor is preferably provided with storage means for storing the codes in the sequence in which they are read, and with program means for analysing the sequence to determine any defect.

The microprocessor may comprise the micro-computer sold under the name EPSON HX-20, which is a portable computer powered by a rechargeable battery pack. This computer includes a small printer and liquid crystal display, and it can be interfaced with a conventional printer and VDU.

The reading means may be the Hewlett Packard HBCS 2400 which is a standard wand for reading bar codes; this has a resolution of about 0.13 mm. When using this wand the separation between the code and the wand during reading should preferably be maintained between 4 mm and 4.75 mm, most preferably at substantially 4.25 mm.

The code may be a form of bar code, preferably adapted to be of circular configuration. Any standard bar code can be used, such as. Code 39, Interleaved 2 of 5, Codabar, Modified Plessey and EAN/UPC; Interleaved 2 of 5 is favoured for reasons of economy.

A bar code ROM can be provided for interpreting the bar code read by the reading means. A pre-programmed chip is available which can be plugged into the back of the EPSON HX-20.

The arrangement of the first and second support means may be such that the reading means can scan the codes on the testing elements from above or below the mounting tray. When the reading means is adapted to scan the testing elements from below, the tray may be provided with a transparent base, or may be provided with a slot extending along the tray base and arranged such that the reading means can be moved along the diameter of the testing elements.

In a preferred construction the guide means includes at least one guide rail and the second support means includes a carriage for mounting the reading means to the or each guide rail.

Preferably adjustment means is provided for adjusting the second predetermined position relative tO the first predetermined position. The adjustment means may comprise a micrometer. The second axis is desirably substantially transverse to the first axis.

Alternatively, it is possible for the reading means to be stationary and for the testing elements to be moved. Also, it is possible for the adjustment means to be provided on the first support means.

The Hewlett Packard HBCS 2400 is, in fact, provided with a tip which spaces the reading head automatically at about 4.25 mm. However, in the above embodiment this tip is removed, since the required spacing can be set using the apparatus.

In order to read the circular code the reading means must pass over the centre of the code. A particular advantage of the circular code is that each code is read twice and this provides a useful check on the accuracy of the code which had been read.

In an alternative embodiment the first and second support means may be dispensed with.

The receptacle may include a removable cover. The receptacle is preferably provided with means to hold the testing elements fixedly in position when they have been disposed in the receptacle. The holding means may comprise a resiliently deformable element such as a foam rubber strip; the holding means may be provided on the cover.

Advantageously the base of the receptacle is provided with a slot which can receive at least a portion of the reading means.

The slot is arranged such that when the testing elements are placed face downwards in the receptacle the codes can be read by the reading means through the slot. The slot preferably extends continuously along substantially the entire length of the receptacle.

The width of the slot and the thickness of the base are selected such that when the reading means is received in the slot, the reading means is automatically spaced from the testing elements by the necessary distance.

It should be noted that when the holding means is provided, the reading means, such as the Hewlett Packard HBCS 2400 can be used with its tip. In this case the tip glides along the surface of the testing elements and automatically spaces the reading head by the required distance. The holding means ensures that the reading elements cannot be moved under the pressure exerted by the tip.

The holding means can, of course, be employed in the embodiment which uses first and second support means.

Although the apparatus according to the invention is especially useful in conducting the FM 100 Hue test, it is also useful in the testing of other eye defects. For example, the apparatus can readily be adapted for use with the Lanthony test ("Semiologie Clinique de la Saturation Chromatique" by P. Lanthony in La Clin. Opthal. (revu medicale), volume 3, 1977, pages. 47 to 106), and the Lightness Discrimination Test ("The Lightness Discrimination Test" by G. Verriest et al in Bull. Soc. Belge Ophthal. volume 183, 1979, pages. 162 to 180).

In general, the apparatus according to the invention can be used in any test of visual function or eye defect where a subject is required to place a number of testing elements in a selected order.

The apparatus according to the invention enables the FM 100 Hue test and other tests to be carried out much more quickly than usual. The apparatus is also much cheaper than computerised systems for the FM 100 Hue test which have been previously available.

Also, since there is no need for an operator to input any information concerning the results of the test, the risk of operator errors is minimised.

According to another aspect of the invention there is, provided a testing element for use in quantifying visual function defects comprising a body having a surface provided with a selected visual stimulus and with identification means comprising a machine readable code for uniquely identifying the selected visual stimulus.

Advantageously the code is such that it can be read by reading means passed over the surface of the element in any direction.

Preferably the code comprises a plurality of substantially circular lines of predetermined thickness and spacing said predetermined thickness and spacing being such as to identify uniquely the selected visual stimulus on the surface of the testing element.

According to another aspect of the invention there is provided an article having identification means in the form of a code which comprises a plurality of substantially circular lines of predetermined thickness and spacing said predetermined thickness and spacing being such as to identify the article uniquely.

Each particular configuration of the thickness and spacing of the lines may correspond to a particular article. In this way the article may be uniquely identified by means of the code provided thereon.

The article may be a testing element of the type described above. Alternatively the article could be a consumer item available in a retail outlet, for example.

As explained above, the circular bar code enables the code to be read from any direction in a given plane, and provides an extra check that the code has been read correctly.

BRIEF DESCRIPTION OF THE DRAWINGS

Reference is now made to the accompanying drawings, in which:

FIG. 1 is a front view of a testing element according to the invention;

FIG. 2 is a rear view of a testing element according to the invention;

FIG. 3 is a perspective view of one embodiment of apparatus for testing eye defects according to the invention;

FIG. 4 is a sectional view of the apparatus shown in FIG. 3;

FIG. 10 is a sample of a printout obtained using the apparatus according to the invention.

DESCRIPTION OF THE PREFERRED EMBODIMENTS

Figure 5:
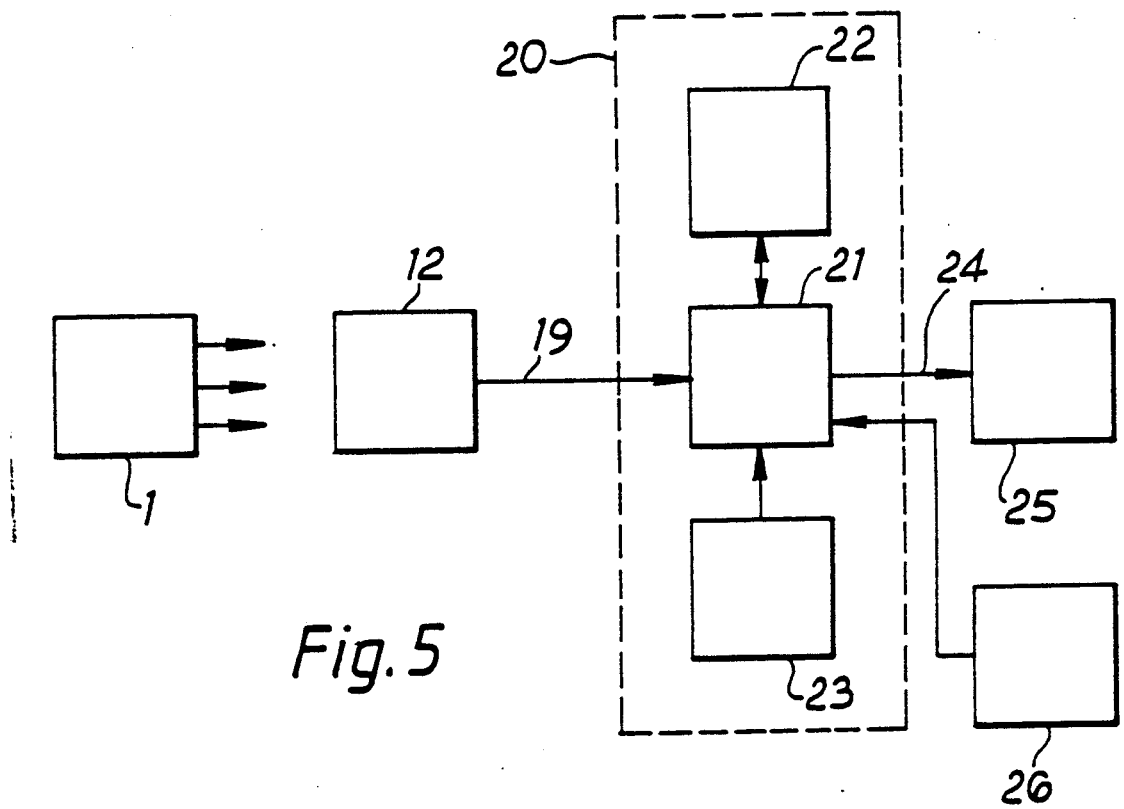
FIG. 5 is a schematic block diagram of apparatus according to the invention.

Referring to FIGS. 1 and 2 a testing element comprises a disc generally designated 1 in the form of a body having a surface 2 provided with a front face 3 and an opposite rear face 4.

On the front face 3 a visual stimulus. 5 is provided. In the embodiment shown the stimulus 5 comprises a coloured region for use in the FM 100 Hue test.

On the rear face 4 identification means in the form of a code generally designated 6 is provided. The code 6 comprises a plurality of lines 7 and each line 7 is of substantially circular configuration.

The lines 7 are dimensioned and spaced to identify uniquely the visual stimulus. 5 on the face 3 of the testing element 1.

When the testing elements are being used in the FM 100 Hue test there are a total of 85 testing elements 1 each of which is provided with a different colour on the face 3 and with a different code 6 on the face 4. The code 6 identifies uniquely the colour on the face 3.

The procedure for the test itself is well known and is described in detail in the references cited above. Briefly, the subject being tested is asked to arrange certain of the testing elements 1 in a selected order on a testing element receptacle in the form of a tray 11 (see FIG. 4) between two end testing elements. The subject should endeavour to place the elements 1 in an order which forms a regular colour series between the two end testing elements. The subject has to complete the sequence four times using different end elements each time. The test is carried out for each eye of the subject. The particular order which the subject selects can be analysed (using known techniques which are described in the cited references) to diagnose colour blindness in the subject.

After the subject has arranged the testing elements 1 on the tray 11 in a selected order then they can be placed in the apparatus shown in FIGS. 3 to 5.

This apparatus comprises a base plate S having first support means which includes two support elements in the form of rails 9 and 10 provided thereon. The rails 9 and 10 are arranged so that the tray 11 (which is also part of the first support means) can be arranged at an angle (preferably about 15°) to the plane of the base plate 8. In FIG. 3 the tray 11 has been omitted for clarity.

Reading means in the form of a light pen 12 (for example the Hewlett Packard HBCS 2400 with the tip removed) is mounted to second support means which includes a carriage 15 and guide means in the form of two spaced substantially parallel guide rails 16 and 17 which are disposed along a first axis. The light pen 12 is mounted to a micrometer gauge 13 on the carriage 15 by a mounting 14. The micrometer gauge 13 enables the light pen 12 to be adjusted vertically towards and away from the testing elements 1 in the tray 11, along a second axis substantially transverse to the first axis. The rails 8 and 9 are substantially parallel to the first axis.

The carriage 15 is slidably mounted to the rails; 16 and 17 and is slidable in a horizontal direction substantially parallel to the first axis.

Each end of the rails 16 and 17 is fitted to end supports 18 which support the rails 16 and 17 above the base plate 8.

A wire 19 is provided for connecting the light pen 12 to a microprocessor 20 (see FIG. 5), such as the EPSON HX-20.

The microprocessor 20 includes program means 21, storage means. 22 and a decoder 23. The output 24 of the microprocessor 20 is connected to a printer 25. The microprocessor 20 is also connected to a keyboard 26. If desired, the printer 25 and keyboard 26 can be integral with the microprocessor 20.

After the tray 11 has been supported by the support rails 9 and 10 such that the elements 1 extend in a row substantially parallel to the first axis, the light pen 12 is adjusted vertically towards the elements 1 until the optimum distance from the elements has been achieved; typically for the HBCS 2400, this distance would be about 4.25 mm.

The light pen 12 and carriage 15 are then slid horizontally along the guide rails 16 and 17 and the code 6 on each element 1 are read twice. The microprocessor 20 stores the codes 6 which are read in the storage means 22 and checks that the codes are read accurately. It should be noted that the second time the code is read in the reverse direction to the first time; the microprocessor 20 can be programmed to allow for this.

When the code 6 of each testing element 1 has been read the microprocessor 20 analyses the data. The micro-processor 20 may be connected to a graph plotter (not shown) to print a linear histogram of the results, or to print a polar graph of the results, as well as to the printer which prints a summary of the numerical data.

Another embodiment of apparatus according to the invention is shown in FIGS.. 6 and 7.

Figure 6:
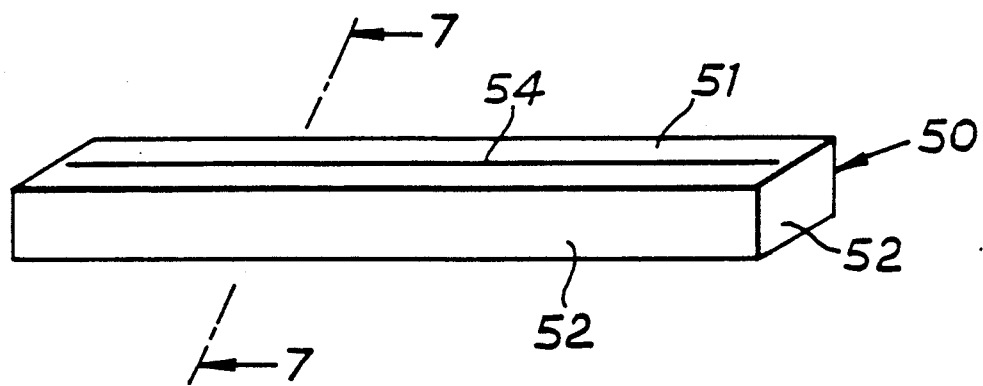
FIG. 6 is a perspective view of the underside of a further embodiment of apparatus according to the invention.
Figure 7:
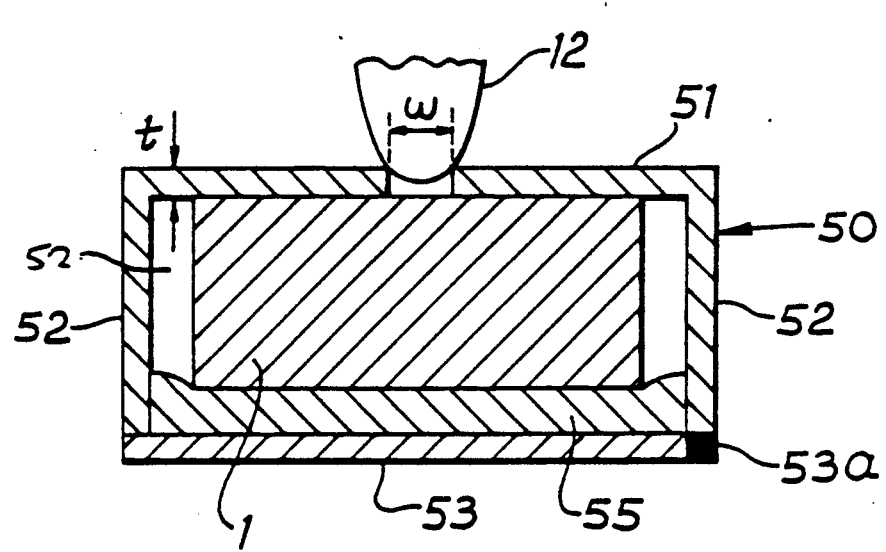
FIG. 7 is a sectional view on an enlarged scale, along lines 7—7 of FIG. 6.

In FIGS. 6 and 7 the testing apparatus includes an elongate receptacle 50 within which the testing elements 1 are disposed in a row in the order selected by the patient.

The receptacle 50 has a base 51, side walls 52 and a cover 53. The cover 53 is hingedly mounted, by hinge 53a, to one of the side walls 52 so that it can be opened and closed.

The base 51 includes an elongate slot 54 which extends substantially along the entire length of the receptacle 50..The slot has a width "w", and the base has a thickness "t".

The cover is provided with holding means in the form of a foam strip 55.

In this embodiment the tip may be left on the pen 12. In this case it is possible for the spacing of the light pen 12 to be achieved using the tip, rather than by accurate dimensioning of the slot 54 and the base thickness.

It is further possible to replace the base 51 with a transparent base which is not provided with the slot 54. In this case the tip of the pen 12 would be removed, and the thickness of the transparent base would be about 4.25 mm.

The apparatus shown in FIGS. 6 and 7 is used as follows.

Firstly the receptacle 50 is arranged supported on the base 51 with the cover 53 open. Two testing elements 1 are disposed at opposite ends of the receptacle 50, and the patient is asked to arrange the remaining testing elements 1 in the receptacle 50. This procedure for the FM 100 Hue test is basically the same as has been described in respect of FIGS. 3 and 4.

The testing elements, 1 are placed with their faces 4 on the base 51 and the faces. 3 facing upwardly. The elements 1 are arranged so that the centre of the code 6 is disposed substantially midway across the width of the slot 54.

When all the elements 1 have been disposed in the receptacle 50, the cover 53 is closed and the foam strip 55 deforms against the elements 1, thereby holding them rigidly in position.

The receptacle 50 is then turned over to the position shown in FIGS. 6 and 7.

The light pen 12 is then placed in the slot 54 and is slid by hand along the slot thereby reading the codes 6 in the selected sequence. The width "w" and thickness "t" of the slot 54 and base 51 respectively are selected so that when the light pen 12 is disposed in the slot 50 it is automatically spaced from the face 4 of the elements 1 by the necessary distance. With the Hewlett Packard HBCS 2400 this distance is about 4.25 mm.

The remainder of the apparatus for this embodiment is the same as shown in FIG. 5.

Figure 8:
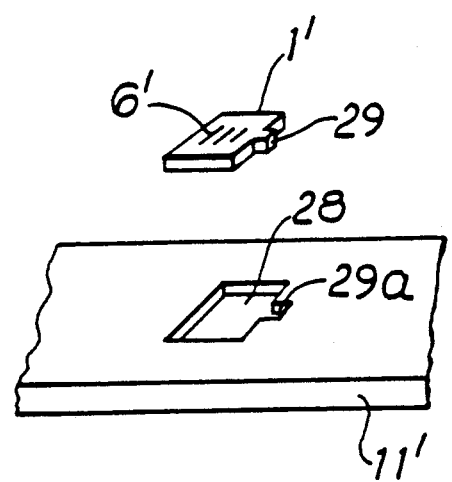
FIG. 8 is a plan view of part of a further embodiment of apparatus.

Part of another embodiment is, shown in FIG. 8.

FIG. 8 shows a receptacle in the form of a tray 11' for a testing element 1' having a linear bar code 6'; the element 1' is substantially rectangular.

The tray 11' is, provided with a recess 28 for receiving the element 1'. Alignment means in the form of formations 29 and 29a are provided on the element 1' and tray 11' respectively. The alignment means ensures that the element 1' can only be received in the recess 28 in a predetermined orientation, so that the light pen 12 can be swept across the row of elements 1' in a single sweep.

Figure 9:
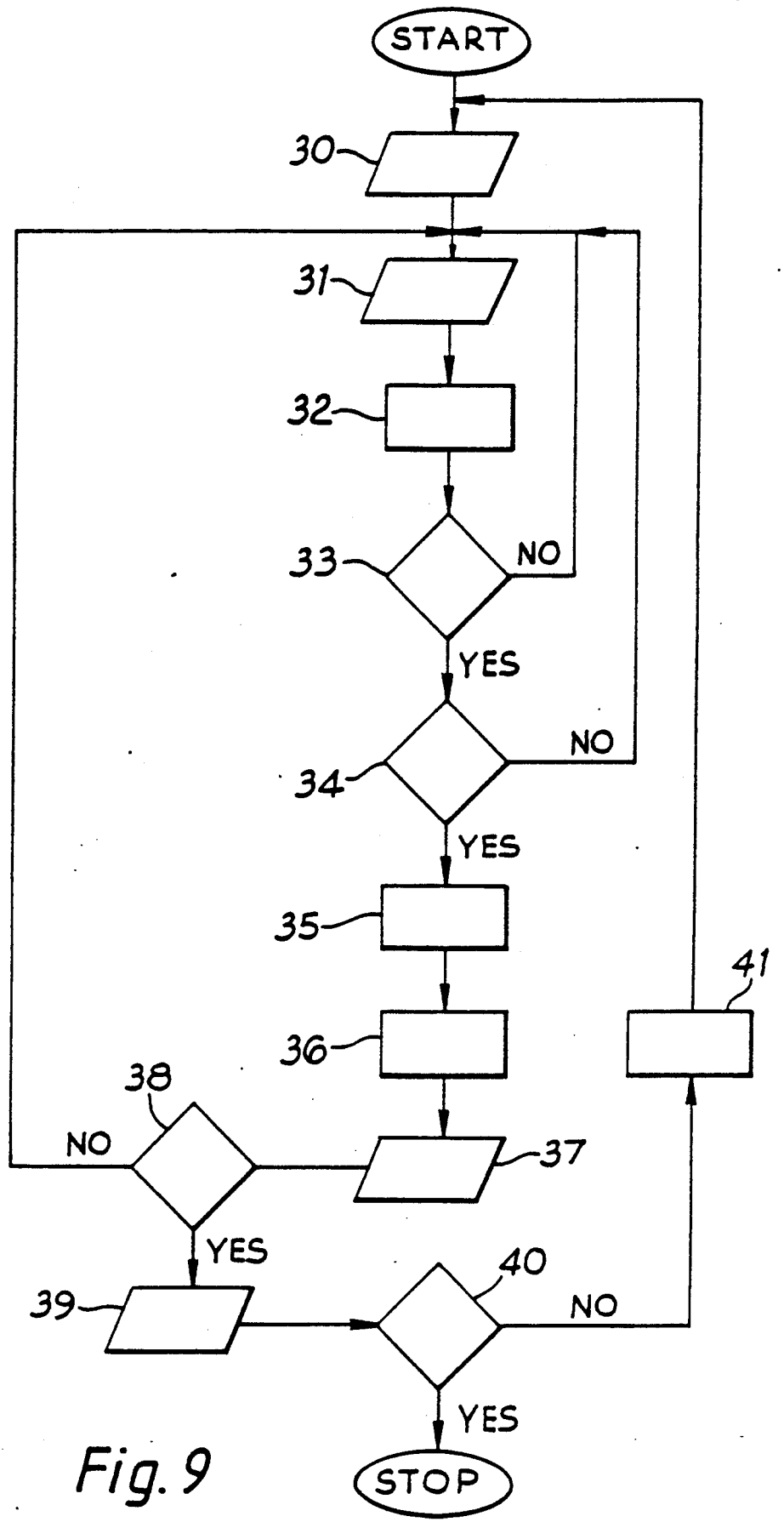
FIG. 9 is a flow chart showing the operation of a microprocessor used with the apparatus according to the invention.

FIG. 9 is a flow chart showing the steps involved in the operation of the microprocessor.

Input step 30 indicates an input into the micro-processor through the keyboard 26. The data inputted may include, for example, the subject's name, hospital number, and date of birth.

Input step 31 indicates input from the light pen 12. The codes 6 of the testing elements 1 in the tray 11 are read sequentially from one end to the other and the results are stored in the storage means 22.

At step 32 the program means. 21 calculates whether each code 6 has been read correctly for each testing element 1. Since each code is read twice, a double check on the accuracy is automatically obtained.

At decision step 33 the program means 21 considers whether all the codes 6 have been read correctly. If not, then the program means. 21 returns to input step 31. If yes, then the program means. 21 moves to decision step 34.

At decision step 34 the program means 21 considers whether the test has been completed i.e. whether all four sequences for the eye being tested have been read. If no, the program means 21 returns to input step 31. If yes, the program means, 21 moves on to step 35.

At the step 35 the program means. 21 decodes the code 6 using the decoder 23 into a form which it can use to perform the FM 100 Hue test calculations. At step 36 the program means. 21 performs these calculations.

At output step 37 the program means. 21 outputs the results of the test for the eye tested, and moves along to input step 38.

At decision step 38 the program means. 21 asks whether both eyes have been tested. If no, the program means. 21 returns to step 31 to conduct the test for the second eye. If yes, the program means moves to input step 39. It should be noted that when the program means reaches step 36 for the second eye it performs additional calculations which make a comparison between the eyes and the results of these are printed at step 37.

At input step 39 the operator inputs on the keyboard 26 whether all the subjects have been tested.

At decision step 40 the program means! 21 evaluates whether all the subjects have been tested on the basis of the input at input step 39. If no, then the program means 21 moves to step 41 where the random access memory is cleared, and then moves back to step 30. If yes, the program means 21 stops.

EXAMPLE

The test was carried out by one of the inventors, Dr. Reeves, using the apparatus described with respect to FIGS. 1 to 4.

The program means. 21 was first started, and Dr. Reeves' personal details were inputted using the keyboard 26.

Dr. Reeves then placed the testing elements 1 in the tray 11 in an order which appeared to him, using his left eye, to provide a smooth variation in colour from one end to the other of the row of elements 1. The elements 1 were placed in the tray 11 with the face 4 facing upwards.

Following this Dr. Reeves placed the tray on the rails 9 and 10 and adjusted the light pen 12 to the correct position using the micrometer gauge 13.

The carriage 15 was then slid along the rails 16 and 17 from one end of the tray to the other so that the codes 6 on each element 1 were read sequentially by the light pen 12.

This test was repeated for four separate series of testing elements, each set of testing elements 1 having different end elements. The program means. 21 then calculated the results for the left eye and the results (not shown) were printed.

The test as a whole was then repeated using the right eye, and the new sequence of codes 6 on the testing elements 1 was read by the light pen 12.

The program means 21 then calculated the results for the right eye and made a printout on the printer 25. A sample of the printout is illustrated as FIG. 9.

The printout includes a histogram and also a number of calculated quantities. The principles involved in evaluating the results of the FM 100 Hue test are well described in the references cited above. The total error score in the printout is the sum of the partial error scores for each test element position for the whole test.

The 5% and 1% confidence limits are explained further in the Verriest reference cited above.

The error scores for Box 1, 2, 3 and 4 (i.e. the results for each of the four separate series of testing elements) are described in detail in "A modified 100 hue test for use in the investigation of glaucoma" (by Connolly, C. P. et al in Docum. Ophthal. Proc. Series, p 425–428, 1982, Vol 33, Junk, The Hague, ed. G. Verriest).

The subjects' total error score is compared with what would be expected for a person of the his age, to determine whether or not it exceeds the 5% or 1% confidence limits. Based on this a result of "Normal" and "Abnormal" is printed. In Dr. Reeves' case the result was "Abnormal".

The program then prints the fellow eye score relating to differences between the eyes. This is described in the Verriest reference cited above and in "Inter-eye comparison on the 100 Hue test" (by Aspinal, P. A. in Acta Ophthalmol, Vol 52, pages 307 to 315). In the case of Dr. Reeves, there was no significant difference. It will be appreciated that the printout for the left eye did not include the fellow eye score result.

It will be appreciated that many modifications to the specific embodiments are possible within the scope of the appended claims.

Many different arrangements for the microprocessor 20 are equally useful. For example, the program means 21 could decode the codes 6 as soon as they are read and store the decoded codes in the storage means 22.

On the EPSON HX-20 the program means. 21 can be programmed in the BASIC language. There are many possible forms of program which can be written, using knowledge well known to those skilled in the art.

The embodiment of FIG. 8 can be adapted for use with the apparatus shown in FIGS. 1 to 4 or FIGS. 6 and 7.

We claim:

1. Apparatus for quantifying visual function defects, comprising:
    a plurality of testing elements each having a surface provided with a selected visual stimulus; and with identification means comprising a machine readable code for uniquely identifying said selected visual stimulus;
    means for reading said machine readable code on each element by passing said reading means over surfaces of said testing elements in any direction; and
    microprocessing means adapted to analyze said machine readable code read by said reading means to quantify said visual function defects.

2. Apparatus according to claim 1, wherein the said machine readable code comprises a plurality Of substantially circular lines of predetermined thickness and spacing, said predetermined thickness and spacing being such as to identify uniquely said selected visual stimulus on said surface of said testing element.

3. Apparatus according to claim 1, further comprising an elongate testing element receptacle for receiving said testing elements in a row.

4. Apparatus according to claim 3 wherein said elements and receptacle are provided with alignment means, so that the elements can only be placed in said receptacle in a predetermined orientation.

5. Apparatus according to claim 3, further comprising first support means for supporting said testing elements and receptacle at a first predetermined position.

6. Apparatus according to claim 5, wherein said first support means further comprises at least one support element for supporting said receptacle at said first predetermined position.

7. Apparatus according to claim 3, wherein said receptacle has a base provided with a slot extending along the length of the base, said slot being adapted to receive at least part of said reading means.

8. Apparatus according to claim 7, wherein said slot has a width and said base has a thickness such that when said part of said reading means is received by said slot, said reading means is spaced from said testing elements in said receptacle by a predetermined distance.

9. Apparatus according to claim 3, wherein said receptacle is provided with means to hold said testing elements fixedly in position when in said receptacle.

10. Apparatus according to claim 1, further comprising second support means for supporting said reading means at a second predetermined position.

11. Apparatus according to claim 10, wherein said second support means includes guide means for guiding movement of said reading and said testing elements along a first axis.

12. Apparatus according to claim 11, wherein said testing elements are disposed in a row parallel to said first axis.

13. Apparatus according to claim 11, wherein said guide means includes at least one guide rail and said second support means. includes a carriage for mounting said reading means to the or each guide rail.

14. Apparatus according to claim 10 wherein said second support means includes adjustment means for adjusting said second predetermined position relative to said first predetermined position.

15. Apparatus according to claim 1, wherein said micro-processing means includes storage means for storing said machine readable codes, in the sequence in which they are read, and program means for analysing the sequence of machine readable codes in order to determine any visual function defect.

16. Apparatus according to claim 1, further including printing means for printing the results calculated by said microprocessing means.

17. Apparatus according to claim 1, wherein said reading means comprises a light pen.

18. A testing element for use in quantifying visual function defects, comprising:
    a body having first and second opposite faces;
    a selected visual stimulus being provided on said first face for use in a visual defect test; and
    identification means provided on said second face comprising a machine readable code for uniquely identifying said selected visual stimulus wherein said machine readable code comprises a plurality of substantially circular lines of predetermined thickness and spacing, said predetermined thickness and spacing being such as to identify uniquely said selected visual stimulus on said surface of said testing element.

19. A testing element according to claim 18, wherein the code is such that it can be read by reading means passed over the surface of the element in any direction.

* * * * *